United States Patent [19]

Senaratne et al.

[11] Patent Number: 5,654,486
[45] Date of Patent: Aug. 5, 1997

[54] SYNTHESIS OF CYCLOALKYLDIARYLPHOSPHINES

[75] Inventors: K. Pushpananda A. Senaratne; Arcelio J. Malcolm; Felix M. Orihuela; Hassan Y. Elnagar, all of Baton Rouge, La.

[73] Assignee: Albemarle Corporation, Richmond, Va.

[21] Appl. No.: 620,824

[22] Filed: Mar. 25, 1996

[51] Int. Cl.$^6$ ...................................................... C07F 9/50
[52] U.S. Cl. .................................................................. 568/17
[58] Field of Search ...................................................... 568/17

[56] References Cited

U.S. PATENT DOCUMENTS

| | | | |
|---|---|---|---|
| 2,437,795 | 3/1948 | Walling | 568/17 |
| 4,618,720 | 10/1986 | Bay et al. | 568/17 |
| 4,668,823 | 5/1987 | Murray | 568/17 |
| 4,947,000 | 8/1990 | Meguro et al. | 568/17 |
| 5,354,894 | 10/1994 | Devon | 568/17 |
| 5,527,967 | 6/1996 | Millauer | 568/17 |

OTHER PUBLICATIONS

Aguiar et al., "Lithium Diphenylphosphide: A Convenient Source and Some Reactions", JOC Mar. 1962, vol. 27, pp. 1001–1004.

Toth et al., "Aspects of the Cleavage of Phosphines with Potassium: Synthesis and Reactivity of Lithium and Potassium Bis(p–(dimethylamino)phenyl)phosphide", Organometallics 1990, vol. 9, No. 3, pp. 675–680.

Rossi et al., "Reaction of 1–Bromoadamantane with Diphenylphosphide and Diphenylarsenide Ions by the SRN1 Mechanism. Facile Nucleophilic Substitution at the Bridgehead Position", J. Org Chem 1982, vol. 47, No. 24, pp. 4654–4657.

Aguiar et al., "The Reaction of Lithium Diphenylphosphide and Simple Aryl Halides", Aug. 1963, vol. 28, pp. 2091–2093.

Tsvetkov et al., "A Simple Synthesis and Some Synthetic Applications of Substituted Phosphide and Phosphinite Anions", Synthesis, Mar. 1986, pp. 198–208.

Hayashi et al., "Catalytic Asymmetric Hydroformylation by the Use of Rhodiumcomplexes of Chiral Bidentate Phosphorus Ligands Bearing Saturated Ring Skeletons", Sep. 1979, Bulletin of the Chemical Society of Japan, vol. 52, No. 9, pp. 2605–2608.

Morrison et al., "Synthesis of Menthyl–and Neomenthyldiphenylphosphine. Epimeric, Chiral, Tertiary Phosphine Ligands for Asymmetric Synthesis", J. Org Chem, vol. 39, No. 2, 1974, pp. 270–272.

Wittenberg and Gilman, "Lithium Cleavages of Triphenyl Derivatives of Some Group Vb Elements in Tetrahydrofuran", J Org Chem vol. 23, pp. 1063–1065, Jul. 1958.

Kuchen and Buchwald, "Reactions of diphenylphosphine Sodium", Angew Chem 69, pp. 307–308 (1957)—Abstract Attached.

*Primary Examiner*—James H. Reamer
*Attorney, Agent, or Firm*—Philip M. Pippenger

[57] ABSTRACT

Partially sterically-hindered cycloalkyl chlorides are reacted with lithium diarylphosphides in inert liquid hydrocarbon reaction media to form cycloalkyldiarylphosphines. Aryl lithium is coproduced. The process makes it possible to avoid, or at least substantially eliminate, the interaction with or cleavage of cyclic ether reaction media such as tetrahydrofuran, previously the solvent of choice for conducting this type of reaction. Also during the conduct of the present process the chloro-substituted cycloalkane does not undergo any appreciable reaction with the coproduced aryl lithium as it is formed. Thus improvements both in yield and quality of the cycloalkyldiarylphosphine product are made possible. A comprehensive three-step process for converting triarylphosphine to cycloalkyldiarylphosphine is also described.

21 Claims, No Drawings

5,654,486

SYNTHESIS OF CYCLOALKYLDIARYLPHOSPHINES

TECHNICAL FIELD

This invention relates to an efficacious process for producing cycloalkyldiarylphosphines from triarylphosphines.

BACKGROUND

Cycloalkyldiarylphosphines constitute a group of chemical products of considerable usefulness as ligands for making noble metal catalysts. Menthyldiphenylphosphine and neomenthyldiphenylphosphine are examples of ligands which impart to transition metal complexes the potential for diastereomeric interactions with unsaturated organic substrates, thus making asymmetric synthesis possible. Note in this connection, J. D. Morrison and W. F. Masler, *J. Org. Chem.*, 1974, Vol. 39, No. 2, pages 270–272. Neomenthyldiphenylphosphine is of particular importance for the preparation of noble metal catalysts useful in the synthesis of certain pharmaceuticals such as naproxen, ketoprofen, ibuprofen, etc.

A known method of generating tertiary phosphines with two aryl groups and a dissimilar third hydrocarbyl group involves coupling a lithium diaryl phosphide with a halohydrocarbon such as benzyl chloride in an ether such as tetrahydrofuran. See A. M. Aguiar, J. Beisler and A. Mills, *J. Org. Chem.*, 1962, Vol. 27, pages 1001–1005. Because the reaction co-produces a reactive aryl lithium coproduct which can complicate synthesis procedures, the authors (Aguiar et al.) developed a method of selectively eliminating this coproduct. They accomplished this by adding to the reaction mass an equivalent amount of tert-butyl chloride to selectively react with the aryl lithium so that isobutylene, aromatic hydrocarbon and lithium chloride are formed. Nevertheless an extra reactant and a concurrent reaction were involved in this approach.

Another complicating factor in the reaction of lithium diaryl phosphide with a halohydrocarbon in tetrahydrofuran is that one or more components in the system tend to interact with the tetrahydrofuran whereby side reactions such as ring cleavage can occur under the conditions used. In addition, the reaction between lithium diaryl phosphide and menthyl chloride is slow and requires prolonged reaction periods, which in turn favors the opportunity for more adverse interaction with the cyclic ether solvent such as ring cleavage to occur.

SUMMARY OF THE INVENTION

In accordance with this invention, certain partially sterically-hindered chloro-substituted cycloalkanes (cycloalkyl chlorides) are reacted with lithium diarylphosphides in suitable hydrocarbon reaction media to form useful cycloalkyldiarylphosphines. Not only does the process of this invention make it possible to avoid, or at least substantially eliminate, the interaction with or cleavage of cyclic ether reaction media such as tetrahydrofuran, but during the conduct of this process the chloro-substituted cycloalkane does not undergo any appreciable reaction with the coproduced aryl lithium as it is formed. Thus this invention makes possible improvements both in yield and quality of the cycloalkyldiarylphosphine product.

In one of its embodiments this invention provides a process of forming a phosphine of the formula $R^1R^2R^3P$ which process comprises reacting an alkali metal diarylphosphide of the formula $Li^{\oplus} \ ^{\ominus}PR^1R^2$ with an alkyl-substituted monochlorocycloalkane of the formula $R^3Cl$ in an inert liquid hydrocarbon reaction medium in which said phosphide is soluble such that said phosphine is formed, wherein $R^1$ and $R^2$ are the same or different aryl groups, and wherein $R^3$ is a mono- or polyalkyl-substituted cycloalkyl group having from 5 to 8 carbon atoms in the ring and where a linear or branched alkyl group of up to about 12 carbon atoms is substituted on one of the ortho positions of the ring. By "soluble" is meant that the reactant is capable of dissolving in the hydrocarbon reaction medium at the reaction temperature being employed, at least to the extent necessary to enable the reaction to proceed at a reasonable reaction rate. The term does not imply that the reactant must be soluble in all proportions, but in general the greater its solubility in the reaction medium, the better.

This invention further provides as one of its embodiments a three-step process of forming a phosphine of the formula $R^1R^2R^3P$, wherein $R^1$, $R^2$ and $R^3$ are as defined above. This process comprises as the first step reacting a triarylphosphine with metallic lithium, in a liquid ether reaction medium in which the phosphine is soluble, in proportions such that a solution of lithium diarylphosphide and aryl lithium in the ether reaction medium is formed. In the second step at least a substantial portion (e.g., at least 80 wt %, and preferably at least 90 wt %, and most preferably substantially all) of the ether reaction medium is replaced by one or more inert liquid hydrocarbons to form a solution of at least a portion of the lithium diarylphosphide along with at least a portion of the aryl lithium. The third step involves reacting the dissolved lithium diarylphosphide with at least one mono- or polyalkyl-substituted 1-chlorocycloalkane having a single 5- to 8-membered ring which is substituted in one of the ortho positions relative to the chloro-substituted carbon atom by a linear or branched alkyl group having up to about 12 carbon atoms, to form a phosphine of the above formula $R^1R^2R^3P$.

Other embodiments and features of this invention will be still further apparent from the ensuing description and appended claims.

FURTHER DESCRIPTION OF THE INVENTION

Lithium Diarylphosphide (LiDAP)

The lithium diarylphosphide used in the processes of this invention can be represented by the formula

where $R^1$ and $R^2$ are the same or different aryl groups, which typically contain up to about 24 carbon atoms each. The aryl groups may have a single ring or a plurality of rings, and include phenyl, 1-naphthyl, 2-naphthyl, 2-biphenylyl, 3-biphenylyl, 4-biphenylyl, acenaphthyl, phenanthryl, tetrahydronaphthyl, and like aromatic groups. The aryl groups can be substituted or unsubstituted, and when substituted can contain one or more substituents inert to metallic lithium, such as one or more: alkyl groups, alkenyl groups, hydrocarbyloxy groups, hydrocarbylthio groups, hydrocarbylcarbonyl groups, hydrocarbyloxyhydrocarbyl groups, dihydrocarbylamino groups, and heteroaromatic groups, and combinations of two or more of these. Preferably, the aryl groups are phenyl groups each of which is either unsubstituted or has up to 3 alkyl substituents having up to about 4 carbon atoms each. Phosphides in which the two aryl groups are the same are preferred, and most preferred is lithium diphenylphosphide. Sodium and/or potassium diarylphosphides can be used in the processes of this invention in lieu of the lithium diarylphosphide. As more fully described in our copending application Ser. No. [Case PI-6957], filed [contemporaneously herewith], the ether cleavage problem does not arise when using sodium and/or potassium diarylphosphides in a reaction with the one or more mono- or polyalkyl-substituted 1-chlorocycloalkane.

Alkyl-Substituted Monochlorocycloalkane (AMCC)

The alkyl-substituted monochlorocycloalkane, also known as an alkyl-substituted cycloalkyl chloride, used in the processes of this invention can be represented by the formula $$R^3Cl$$

where $R^3$ is a mono- or polyalkyl-substituted cycloalkyl group preferably having from 5 to 8 carbon atoms in the ring and where a linear or branched alkyl group of up to about 12 carbon atoms is substituted on one of the ortho positions of the ring. In addition to this required ortho-alkyl substitution, the ring may contain other substituents which are innocuous in the sense that they will not impair or inhibit the desired reaction. While such additional substituents can be in any positions which do not unduly sterically hinder the chlorine atom, such substituents are preferably in the meta or para positions relative to the chlorine substitution. Examples of such innocuous substituents include alkyl groups, alkenyl groups, hydrocarbyloxy groups, hydrocarbylthio groups, hydrocarbylcarbonyl groups, hydrocarbyloxyhydrocarbyl groups, and heteroaromatic groups, dihydrocarbylamino groups, and combinations of two or more of these. Typically in the practice of this invention, this reactant will contain a total of up to about 24 carbon atoms, and preferably up to about 18 carbon atoms, in the molecule. As regards ring size, most preferably the ring is a 6-membered ring. The ortho-alkyl substituent is preferably a secondary alkyl group which most preferably contains up to about 6 carbon atoms. A particularly preferred reactant is menthyl chloride.

Hydrocarbon Solvent

Any inert liquid hydrocarbon reaction medium in which the lithium diarylphosphide and the alkyl-substituted cycloalkyl monochloride reactants are soluble and that exists in the liquid state under the temperature conditions at which it is being used is suitable for use in the conduct of the reaction between these reactants. Preferably the reaction medium should remain in the liquid state at 10° C. or below. The hydrocarbons can be paraffinic, cycloparaffinic or aromatic, or various mixtures or blends of these.

The preferred hydrocarbons are aromatic hydrocarbons which may contain one or more tings and when more than one ting is present, the rings may be condensed or non-condensed rings. There may be more than one alkyl substituent on an aromatic ring(s) so long as the hydrocarbon exists in the liquid state under the conditions being used. The reaction medium may be composed of a single aromatic hydrocarbon such as toluene, o-, m- or p-xylene, ethylbenzene, butylbenzene, 1,2,3,4-tetrahydronaphthalene, etc., or it may be a mixture of aromatic hydrocarbons such as, for example, aromatic naphthas, BTX, aromatic gasoline fractions, a mixture of o-, m- and p-xylene, a mixture of toluene and ethylbenzene, or a mixture of m- and p-xylene and pentaethylbenzene. For best results, at least 50 volume percent of the reaction medium should be composed of one or more liquid aromatic hydrocarbons, substantially the entire balance, if any, most preferably being one or more cycloaliphatic hydrocarbons (preferably predominately or entirely cycloparaffinic hydrocarbons) and/or one or more aliphatic hydrocarbons (preferably predominately or entirely paraffinic hydrocarbons). Small amounts (e.g., 10 volume percent or less) of other solvents, such as ethers, ketones, tertiary amines, esters, etc., may be present without undue sacrifice of the efficacy of the process. Generally speaking, the higher the volume percentage of aromatics in the reaction medium, the better. Thus preferably at least 90 volume percent of the total liquid reaction medium is composed of aromatic hydrocarbons. For toxicological reasons, reasonable care should of course be exercised in minimizing exposure of personnel to aromatic hydrocarbons, especially those containing benzene.

For best results, it is desirable to degas (i.e., remove air or oxygen) from the hydrocarbon solvent before use. This can be accomplished by refluxing the hydrocarbon in the absence of air, or by blowing an inert gas such as dry nitrogen through the hydrocarbon to strip out entrained or dissolved air or oxygen.

Conditions for Reaction between LiDAP and AMCC

The conditions for the reaction between the lithium diarylphosphide and the alkyl-substituted cycloalkyl monochloride need not be severe. Temperatures in the range of between about 40° and about 120° C. will normally suffice. A preferred range is from about 60° to about 100° C. The reaction is preferably performed at atmospheric pressure, although this is not essential. For example, if using a hydrocarbon solvent that has a boiling point below, or boiling range at least in part below, the reaction temperature selected for use in the process, the reaction should be performed under super-atmospheric pressure sufficient to keep the hydrocarbon in the liquid state. Likewise reduced pressure can be employed under suitable circumstances (e.g., use of a high boiling hydrocarbon reaction medium, etc.). Proportions are not critical, but normally will be relatively close to equimolar, e.g., from about 0.8 to about 1.5 mols of the alkyl-substituted cycloalkyl monochloride per tool of the lithium diarylphosphide. The reaction should be conducted under a dry inert atmosphere.

Triarylphosphines and Formation of LiDAP

In one embodiment of this invention, the lithium diarylphosphide reactant is formed by cleaving a triaryl phosphine with lithium in an ether reaction medium.

The triaryl phosphine to be used as the starting material can have aryl groups which are the same or different and at least two of which correspond to $R^1$ and $R^2$ above. Thus the aryl groups used in the practice of this invention typically contain up to about 24 carbon atoms each. For further details, the description of $R^1$ and $R^2$ given above should be referred to.

The lithium is preferably employed in a suitable high surface physical form such as in ribbon form or in small pieces or in a finely-divided state such as a dispersion in an inert liquid.

Any liquid ether reaction medium in which the triarylphosphine is soluble and that exists in the liquid state under the reaction conditions being used is suitable for use in the conduct of the cleavage reaction between the lithium and the triarylphosphine. The ethers may be monoethers or polyethers, they may be saturated or unsaturated, and they may be cyclic or acyclic, but in any case should be free of any functionality that would interfere with or inhibit the desired reaction. Examples of polyethers include 1,2- dimethoxyethane, diglyme, 1,4-dioxane, tetrahydrofurfuryl ethyl ether, tetrahydrofurfuryl n-butyl ether, and similar polyethers. Preferably, the ether is one or more saturated hydrocarbyl monoethers, or one or more a hydrocarbyl monoethers having at least one aromatic group in the molecule. Examples include dialkyl ethers, dicycloalkyl ethers, diaryl ethers, monoalkyl monoaryl ethers, monocycloalkyl monoaryl ethers, monoalkyl monocycloalkyl ethers, and saturated cyclic monoethers, or mixtures of any of these. Particularly preferred are tetrahydrofuran and alkyl-substituted tetrahydrofurans.

For best results, it is desirable to degas (i.e., remove air or oxygen) from the ether before use. This can be accomplished an refluxing the ether in the absence of air, or by blowing an inert gas such as dry nitrogen through the ether to strip out entrained or dissolved air or oxygen.

In conducting this cleavage reaction, the temperature will be maintained in the range of about 15° C. to about 45° C. The reaction is conducted at atmospheric pressure as there is no particular advantage (or harm) in conducting the reaction at reduced or elevated pressures. The ratio of lithium to triaryl phosphine is preferably maintained in the range of about 0.8 to about 1.0 gram mol of triarylphosphine per gram atom of lithium.

Replacement of Ether Reaction Medium by Hydrocarbon Solvent

After completing the above cleavage reaction, the reaction mass is composed mainly of a solution of lithium diarylphosphide, aryl lithium, and the ether reaction medium. The second step of the three step embodiment of this invention involves replacing at least a substantial portion of the ether reaction medium by a hydrocarbon solvent or medium of the type described above. While this operation can be conducted in various ways, a preferred procedure is to distill off at least a substantial portion of the ether, and then mix the pot residue and the hydrocarbon solvent together to form a solution for use in the third step, which is conducted as described hereinabove.

The following example is presented for the purposes of illustration and not limitation.

EXAMPLE

Preparation of Lithium DiphenylPhosphide

A solution of triphenylphosphine (10.0 grams, 0.0381 mol) in dry degassed tetrahydrofuran (THF) (100 mL) is stirred with freshly cut lithium (0.528 grams, 0.0762 gram atoms) under a nitrogen atmosphere for 6–7 hours. Lithium diphenylphosphide (LiDPP) is formed as a red solution. In a reaction performed in this manner, the conversion to LiDPP was >93%.

Replacement of THF Reaction Medium by Toluene

The red THF solution of lithium diphenylphosphide is concentrated under vacuum. To the concentrate remaining in the flask is added about 75 mL of dry degassed toluene.

Preparation of Neomenthyl Diphenyl Phosphine (NMDPP)

The LiDPP solution in toluene is placed in a flame dried flask. To this is added 7.31 grams (0.0419 mol) of menthyl chloride, and the mixture is heated to 65° C. After 20 hours at this temperature, the reaction mass is cooled to room temperature and quenched with water. The organic layer is separated and distilled to remove the solvents. The crude product is then dissolved in refluxing anhydrous methanol and cooled to obtain neomenthyl diphenyl phosphine (NMDPP) as white crystals. In a run performed in this manner without optimization, the recovered yield of NMDPP was 60%.

Each and every publication referred to in any portion of this specification is fully incorporated into this disclosure by reference as if fully set forth herein.

Formulas are used herein for the purpose of clarification and to facilitate discussion. In this connection, it is to be understood and appreciated that the formula given for the lithium diarylphosphides, although depicted in ionic format, should not be construed as requiring ionization of the lithium diarylphosphides at any time during the conduct of the process. Rather, it is intended that the lithium diarylphosphides, and indeed the other specified reactants, are in whatever chemical form they assume or acquire when brought together in the solvent or reaction media and when under the conditions specified for the particular reaction.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process of forming a phosphine of the formula $R^1R^2R^3P$, which process comprises reacting a lithium diarylphosphide with an alkyl-substituted monochlorocycloalkane of the formula $R^3Cl$ in a liquid inert hydrocarbon reaction medium in which said phosphide is soluble such that said phosphine is formed, wherein $R^1$ and $R^2$ are the same or different aryl groups, and wherein $R^3$ is a mono- or polyalkyl-substituted cycloalkyl group having from 5 to 8 carbon atoms in the ring and where a linear or branched alkyl group of up to about 12 carbon atoms is substituted on one of the ortho positions of the ring.

2. A process according to claim 1 wherein said hydrocarbon reaction medium consists essentially of one or more liquid aromatic hydrocarbons.

3. A process according to claim 1 wherein said hydrocarbon reaction medium consists essentially of toluene.

4. A process according to claim 1 wherein $R^3$ is a mono- or polyalkyl-substituted cyclohexyl group having a branched alkyl group occupying one of the positions ortho to the ring carbon atom substituted by the chlorine atom.

5. A process according to claim 1 wherein $R^3$ is a dialkyl-substituted cyclohexyl group in which one of the alkyl groups is a branched alkyl group occupying one of the positions ortho to the ring carbon atom substituted by the chlorine atom.

6. A process according to claim 5 wherein said branched alkyl group is an isopropyl group and the other alkyl group is an unbranched alkyl group occupying a meta or para position relative to the ring carbon atom substituted by the chlorine atom.

7. A process according to claim 1 wherein said alkyl-substituted monochlorocycloalkane is menthyl chloride.

8. A process according to claim 1 wherein the lithium diarylphosphide is a lithium diphenylphosphide in which the phenyl group is either unsubstituted or has up to 3 alkyl substituents having up to about 4 carbon atoms each.

9. A process according to claim 8 wherein the hydrocarbon reaction medium consists essentially of one or more liquid degassed alkylbenzenes, and wherein $R^3$ is a dialkyl-substituted cyclohexyl group in which one of the alkyl groups is a branched alkyl group occupying one of the positions ortho to the ring carbon atom substituted by the chlorine atom.

10. A process according to claim 9 wherein the reaction medium consists essentially of toluene.

11. A process according to claim 10 wherein the alkyl-substituted monochlorocycloalkane is menthyl chloride.

12. A process of forming a phosphine of the formula $R^1R^2R^3P$, wherein $R^1$ and $R^2$ are the same or different aryl groups, wherein $R^3$ is a mono- or polyalkyl-substituted cycloalkyl group having from 5 to 8 carbon atoms in the ring and having one of the ortho positions occupied by a linear or branched alkyl group having up to about 12 carbon atoms, which process comprises:
   a) reacting a triarylphosphine with metallic lithium, in a liquid ether reaction medium in which said triarylphosphine is soluble, in proportions such that a solution of lithium diarylphosphide and aryl lithium is formed;
   b) replacing at least a substantial portion of the ether reaction medium by one or more liquid inert hydrocarbons to form a solution of at least a portion of the lithium diarylphosphide along with at least a portion of the aryl lithium; and
   c) reacting at least a portion of the lithium diarylphosphide, while in hydrocarbon solution along with at least a portion of the aryl lithium, with at least one mono- or polyalkyl-substituted 1-chlorocycloalkane having a single 5- to 8-membered ring which is substituted in one of the ortho positions relative to the chloro-substituted carbon atom by a linear or branched alkyl group having up to about 12 carbon atoms, to form a phosphine of said formula $R^1R^2R^3P$.

13. A process according to claim 12 wherein the aryl groups of the triaryl phosphine are the same, wherein the ether is a saturated cyclic monoether, wherein the hydrocarbon reaction medium consists essentially of one or more aromatic hydrocarbons, and wherein said 1-chlorocycloalkane is a 1-chlorodialkylcyclohexane.

14. A process according to claim 13 wherein the ether is tetrahydrofuran or an alkyl-substituted tetrahydrofuran and wherein the hydrocarbon reaction medium consists essentially of toluene.

15. A process according to claim 14 wherein said 1-chlorocycloalkane is menthyl chloride.

16. A process according to claim 15 wherein the triarylphosphine is triphenylphosphine.

17. A process according to claim 16 wherein the ether is tetrahydrofuran.

18. A process of forming a phosphine of the formula $R^1R^2R^3P$, wherein $R^1$ and $R^2$ are the same or different aryl groups, wherein $R^3$ is a mono- or polyalkyl-substituted cycloalkyl group having from 5 to 8 carbon atoms in the ring and having one of the ortho positions occupied by a linear or branched alkyl group having up to about 12 carbon atoms, which process comprises:
   a) reacting a triarylphosphine with metallic lithium, in a liquid ether reaction medium in which said triarylphosphine is soluble, in proportions such that a solution of lithium diarylphosphide and aryl lithium is formed;
   b) distilling off from the reaction mixture of a) at least a substantial portion of the ether reaction medium to leave a residual product mixture;
   c) dissolving at least a portion of the residual product mixture in a one or more liquid inert hydrocarbons to form a solution of lithium diarylphosphide along with aryl lithium; and
   d) reacting at least a portion of the lithium diarylphosphide, while in hydrocarbon solution along with at least a portion of the aryl lithium, with at least one mono- or polyalkyl-substituted 1-chlorocycloalkane having a single 5- to 8-membered ring which is substituted in one of the ortho positions relative to the chloro-substituted carbon atom by a linear or branched alkyl group having up to about 12 carbon atoms, to form a phosphine of said formula $R^1R^2R^3P$.

19. A process according to claim 18 wherein the triarylphosphine is triphenylphosphine and wherein said 1-chlorocycloalkane is menthyl chloride.

20. A process according to claim 18 wherein the aryl groups of the triaryl phosphine are the same, wherein the ether is a degassed saturated cyclic monoether, wherein the hydrocarbon reaction medium consists essentially of one or more degassed aromatic hydrocarbons, and wherein said 1-chlorocycloalkane is a 1-chlorodialkylcyclohexane.

21. A process according to claim 20 wherein the triarylphosphine is triphenylphosphine, wherein the ether is tetrahydrofuran, and wherein said 1-chlorodialkylcyclohexane is menthyl chloride.

* * * * *